United States Patent

Chambers et al.

[11] Patent Number: 5,792,139
[45] Date of Patent: Aug. 11, 1998

[54] ELECTROSURGICAL INSTRUMENT WITH INTERCHANGEABLE SURGICAL TOOLS

[75] Inventors: Alan L. Chambers, Torrington; Ward R. Cusati, Burlington; Tom H. Merrifield, Bristol; Brian McMorrow, Waterbury; Eric L. Sejourne, Fairfield; Arnold M. Terrill, Thomaston, all of Conn.

[73] Assignee: Ethicon Endo-Surgery, Inc., Cincinnati, Ohio

[21] Appl. No.: 851,554

[22] Filed: May 6, 1997

Related U.S. Application Data

[63] Continuation of Ser. No. 745,115, Nov. 7, 1996, abandoned, which is a continuation of Ser. No. 386,037, Feb. 9, 1995, abandoned, which is a continuation of Ser. No. 160,129, Dec. 2, 1993, abandoned.

[51] Int. Cl.⁶ .................................................. A61B 17/36
[52] U.S. Cl. ............................... 606/41; 606/45; 606/46
[58] Field of Search ............................ 606/37–42, 45–52, 606/205–208; 604/21, 22

[56] References Cited

U.S. PATENT DOCUMENTS

| | | |
|---|---|---|
| 1,740,174 | 12/1929 | Hevern . |
| 1,971,024 | 8/1934 | Wappler . |
| 3,629,786 | 12/1971 | Reynolds et al. . |
| 4,016,881 | 4/1977 | Rioux et al. . |
| 4,032,738 | 6/1977 | Esty et al. . |
| 4,347,842 | 9/1982 | Beale . |
| 4,823,791 | 4/1989 | D'Amelio et al. ................. 606/50 |
| 4,898,574 | 2/1990 | Uchiyama et al. . |
| 4,924,851 | 5/1990 | Oginer et al. . |
| 4,936,842 | 6/1990 | D'Amelio et al. . |
| 5,011,493 | 4/1991 | Sleister . |
| 5,100,402 | 3/1992 | Fan . |
| 5,176,702 | 1/1993 | Bales et al. ................. 606/208 |
| 5,186,714 | 2/1993 | Boudreault et al. . |
| 5,195,958 | 3/1993 | Phillipps . |
| 5,195,959 | 3/1993 | Smith . |
| 5,197,948 | 3/1993 | Ghodsian . |
| 5,197,963 | 3/1993 | Parins . |
| 5,230,704 | 7/1993 | Moberg et al. . |
| 5,254,117 | 10/1993 | Rigby et al. . |
| 5,258,006 | 11/1993 | Rydell et al. ................. 606/205 |
| 5,273,524 | 12/1993 | Fox et al. . |
| 5,306,237 | 4/1994 | Clement et al. . |
| 5,312,332 | 5/1994 | Bales et al. . |
| 5,322,503 | 6/1994 | Desai ................. 606/49 |
| 5,324,254 | 6/1994 | Phillips . |
| 5,334,140 | 8/1994 | Phillips . |
| 5,334,198 | 8/1994 | Hart et al. ................. 606/52 |
| 5,342,357 | 8/1994 | Nardella . |
| 5,342,391 | 8/1994 | Foshee et al. ................. 606/205 |
| 5,401,274 | 3/1995 | Kusunoki ................. 606/41 |
| 5,480,409 | 1/1996 | Riza ................. 606/205 |
| 5,562,640 | 10/1996 | McCabe et al. . |
| 5,607,391 | 3/1997 | Klinger et al. . |

OTHER PUBLICATIONS

Sales Literature–Valleylab Laparoscopic Instrumentation.
Sales Literature–MIS Multifunction Pistol Grip Handle with Modular Laparoscopic Electrosurgical Probes.

*Primary Examiner*—Michael Peffley
*Attorney, Agent, or Firm*—Bernard E. Shay

[57] ABSTRACT

A multi-functional surgical instrument having an interchangeable surgical tool removeably, rotatably attached to a handle. An axially moveable sheath on the surgical tool is moveable from a retracted first position wherein an electrosurgical electrode is exposed to an extended second position wherein the sheath covers the electrosurgical electrode. Both the interchangeable surgical tools and the handle are sterilizable and disposable.

8 Claims, 4 Drawing Sheets

ELECTROSURGICAL INSTRUMENT WITH INTERCHANGEABLE SURGICAL TOOLS

This is a continuation of application Ser. No. 08/745,115, filed Nov. 7, 1996 (now abandoned), which is a continuation of application Ser. No. 08/386,037, filed Feb. 9, 1995 (now abandoned) which is a continuation of application Ser. No. 08/160,129, filed Dec. 2, 1993 (now abandoned).

BACKGROUND OF THE INVENTION

This invention relates generally to disposable electrosurgical instruments and more particularly to electrosurgical instruments used to perform laparoscopic surgical procedures.

In one type of current disposable electrosurgical instrument, the cutting electrode is fixedly attached to the handle of the instrument. If a different electrode is needed, a second complete instrument must be used. In another type of disposable surgical instrument, removable electrodes are used, but the electrode is fixedly attached to the handle of the instrument. If the orientation of the electrode is incorrect, the surgeon must rotate the entire instrument including his hand. This can result in his hand being in an awkward position.

The foregoing illustrates limitations known to exist in present disposable electrosurgical instruments. Thus, it is apparent that it would be advantageous to provide an alternative directed to overcoming one or more of the limitations set forth above. Accordingly, a suitable alternative is provided including features more fully disclosed hereinafter.

SUMMARY OF THE INVENTION

In one aspect of the present invention, this is accomplished by providing a multi-functional surgical instrument comprising: a handle; an interchangeable surgical tool removeably, rotatably attached to the handle; and means for indexing the interchangeable surgical tool to a plurality of discrete radial positions.

The foregoing and other aspects will become apparent from the following detailed description of the invention when considered in conjunction with the accompanying drawing figures.

BRIEF DESCRIPTION OF THE DRAWING FIGURES

DETAILED DESCRIPTION

Figures 1, 3:
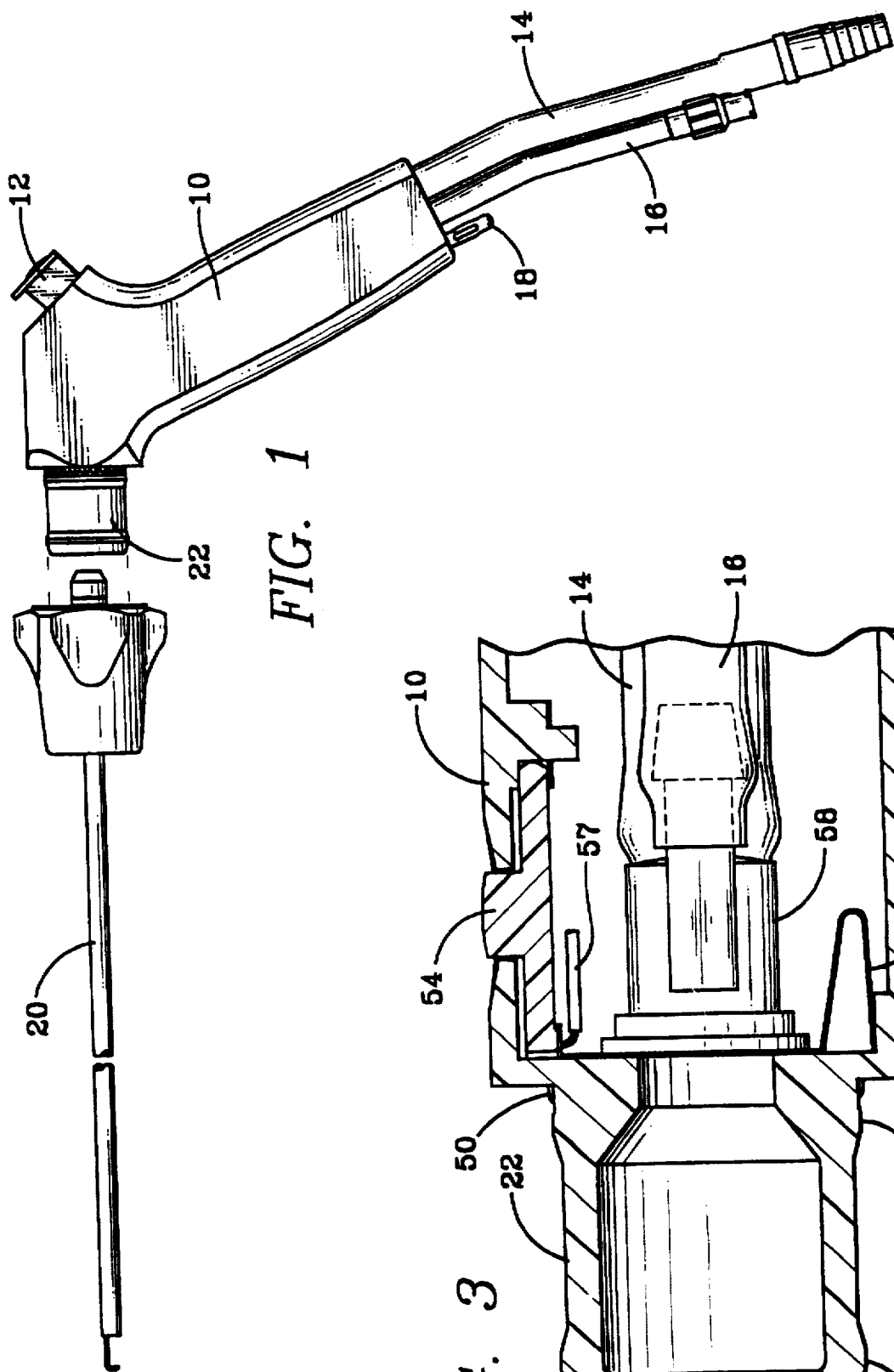
FIG. 1 is a side view of a one embodiment of a surgical handle and removable surgical tool.
FIG. 3 is a partial cutaway top view of the upper portion of the handle shown in FIG. 1.

FIG. 1 shows a side view of a multi-functional surgical instrument comprised of a handle 10 and a removable surgical tool 20. The surgical tool 20 is rotatably attached to the handle 10. In addition to a pistol grip handle 10 shown in the FIGURES, a straight shaped pencil grip handle may also be used with the removable surgical tool 20.

Figure 2:
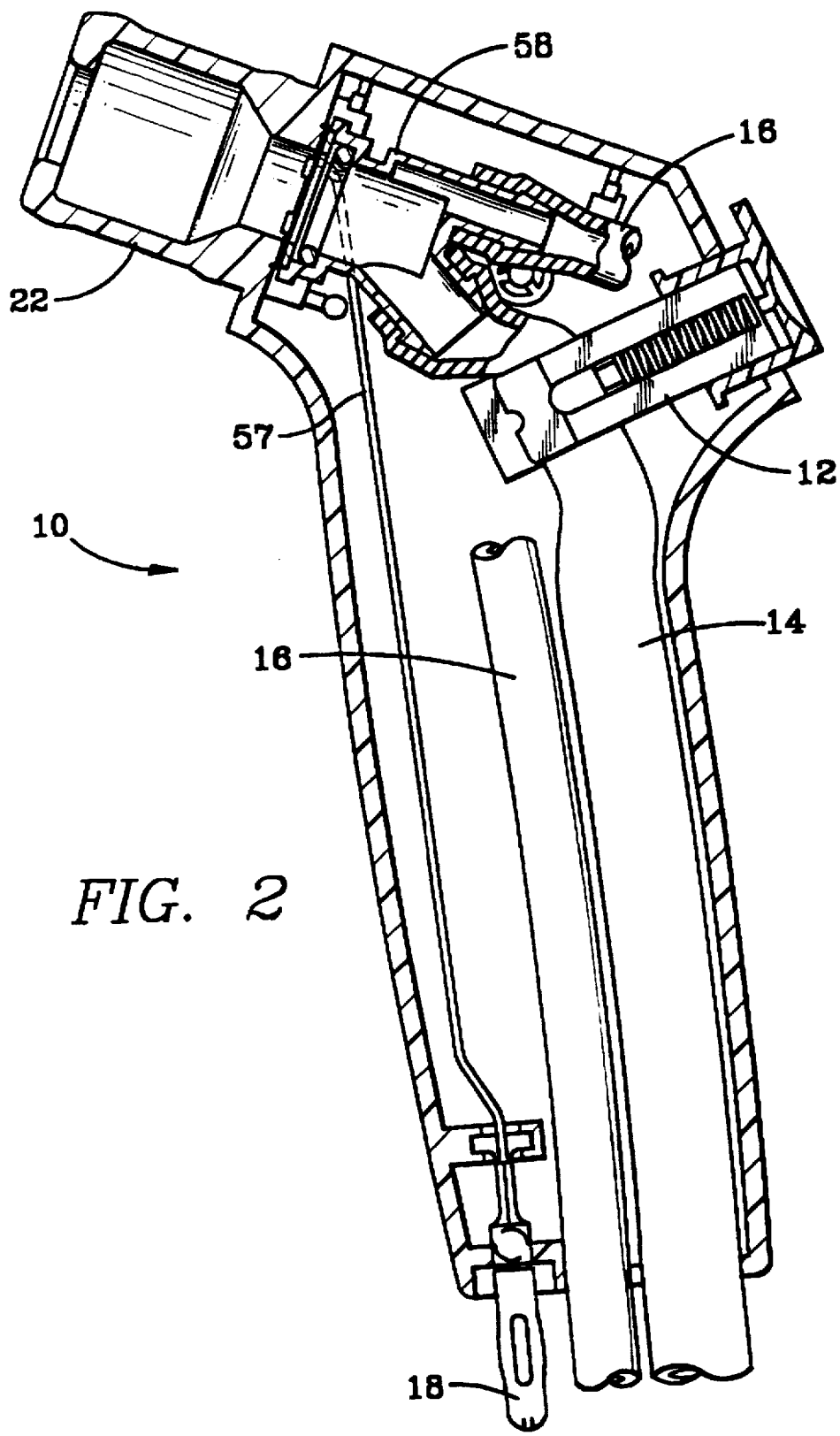
FIG. 2 is cross-sectional view of the handle shown in FIG. 1.

A suction hose 14 and an irrigation hose 16 are located within the handle 10. Both hoses 14, 16 extend from the handle 10 and are terminated with connector fittings which allow the multi-functional surgical instrument to be connected to sources of suction and irrigation. The hoses 14, 16 pass through suction and irrigation control valves 12 and are connected to a manifold 58, shown in FIGS. 2 and 3. The manifold 58 connects the suction and irrigation hoses 14, 16 to the surgical tool 20. Preferably, the suction and irrigation control valves 12 are normally closed valves which release pinched hoses 14, 16 to an open condition when operated.

Attached to the handle 10 is an electrical connector 18 which is connected to an electrosurgical generator (not shown). The embodiment shown in the FIGURES uses an external foot controlled switch (not shown) to control the application of voltage to the electrical connector 18. An alternate embodiment uses a control switch mounted in the handle 10 to select between applying cutting voltage and cauterizing voltage to a surgical tool electrode tip 40. Positioned in the handle 10 is an electrical conductive releasable latch 56 which engages with a groove 35 on an electrode adapter 34 which is part of the surgical tool 20. The releasable latch 56 contains a spring like bent portion on one side which provides a spring force to bias the latch into engagement with the surgical too 20. A release button 54 is used to disengage the releasable latch 56 from the groove 35 to release the surgical tool 20 from the handle 10. The electrical connector 18 is connected to the electrically conductive releasable latch 56 by a short section of wire 57.

A tool attachment extension 22 extends outwardly from the handle 10. Two axial detents 52 are located on the outer peripheral surface of the tool attachment extension 22. A plurality of ratchet teeth or radial detents 50 are also located about the outer peripheral surface of the extension 22. These ratchet teeth 50 are positioned adjacent the main part of the handle 10.

Figure 4:
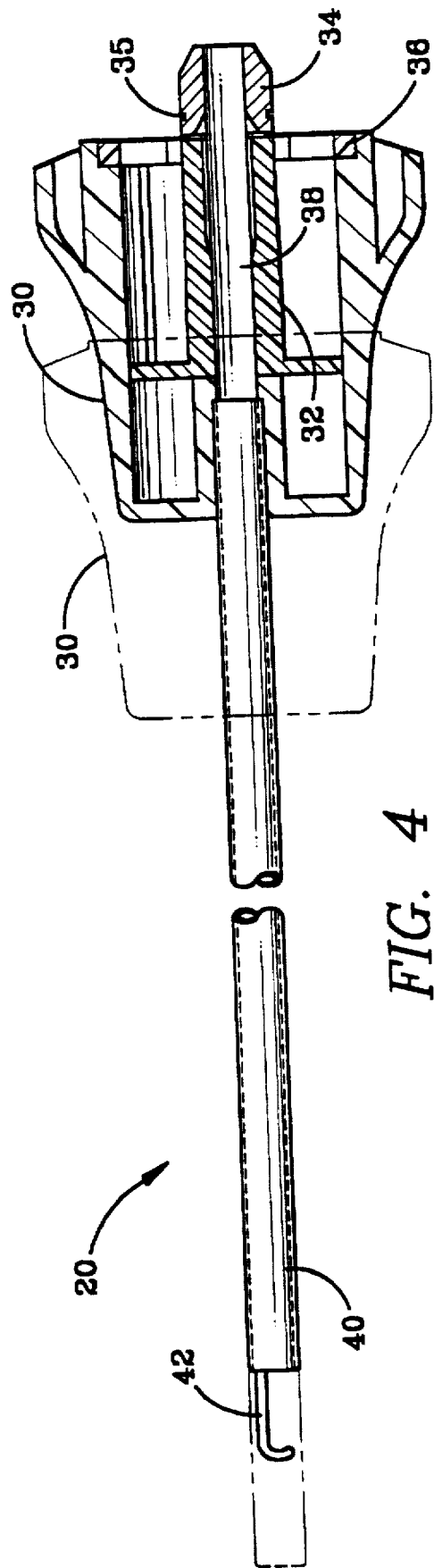
FIG. 4 is a partial cross-section of the removable surgical tool shown in FIG. 1, showing the surgical tool in a retracted position and an extended position.
Figure 6:
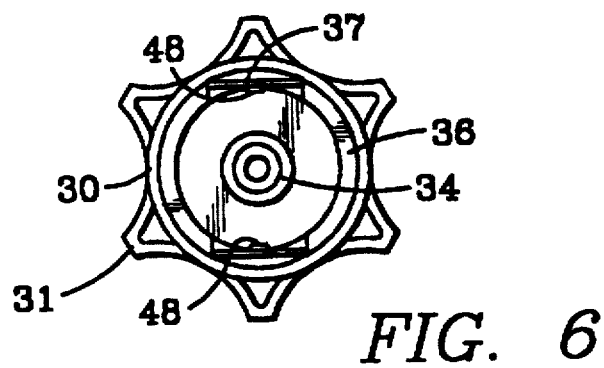
FIG. 6 is end view of the removable surgical tool shown in FIG. 1.
Figure 5:
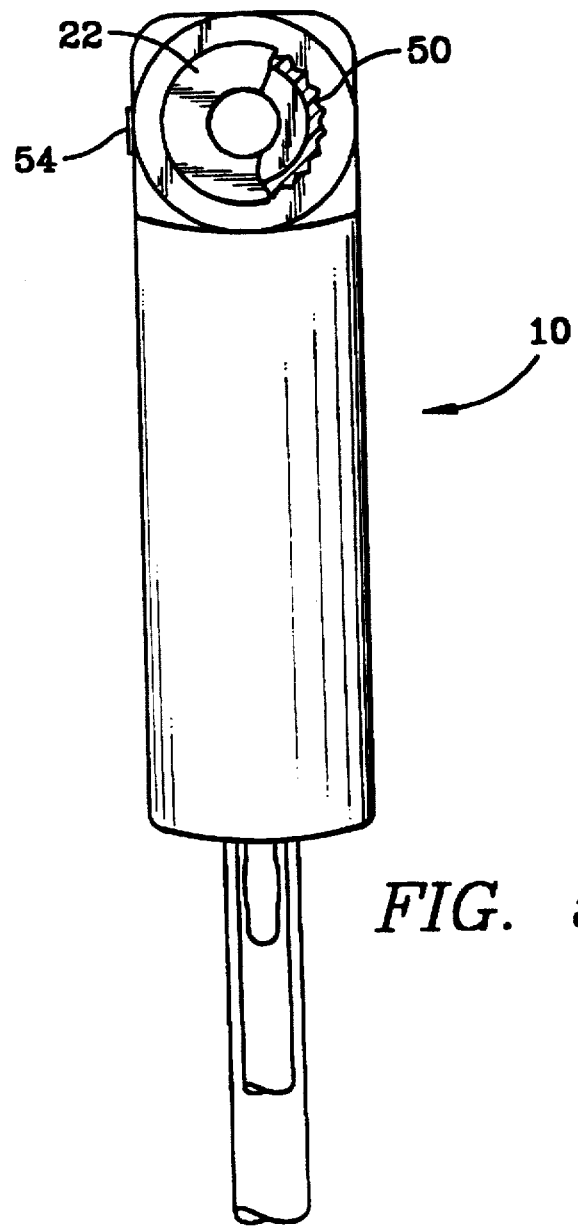
FIG. 5 is a front view of the handle shown in FIG. 1, showing the details of the radial indexing detents.

FIGS. 4 and 6 illustrate some of the details of the surgical tool 20. Shown in all of the FIGURES is a hook probe surgical tool having a 34 cm length and a 5 mm diameter. Surgical tools of other shapes, lengths and diameters may be interchangeably used with the handle 10. One version of the surgical tool is used only for suction and irrigation. This particular tool does not include an electrosurgical electrode.

The surgical tool 20 is comprised of three main parts, an electrode 38, an axially moveable sheath 42 and a tool nose piece 30. A plurality of scallop shaped finger holds 31 are formed in the outer surface of the tool nose piece 30. The electrode 38 is a tubular electrode having a central bore therethrough. An electrode tip 40 is connected to one end of the electrode 38. The other end of the electrode 38 is connected to barrel sleeve and an electrically conductive electrode adapter 34. The latch engaging groove 35 is located in the outer peripheral surface of the electrode adapter 34. The electrode adapter 34 has a bore therethrough. The suction and irrigation hoses 14, 16 are in fluid communication with the distal end of the surgical tool 20 through the manifold 58, electrode adapter 34 and the tubular electrode 38.

An electrically conductive path is formed from the electrical connector 18 through the wire 57, the releasable latch 56, the electrode adapter 34, the electrode 38 to the electrode tip 40 where the current can be applied to either cut or cauterize tissue.

A nonconductive sheath 42 surrounds the electrode 38 and electrode tip 40. The sheath 42 is fixedly attached to the tool nose piece 30. Both the sheath 42 and nose piece 30 are axially moveable relative to the electrode 38 and electrode tip 40. A pair of spring bars 37 are attached to an inner surface of the nose piece 30. The spring bars 37 engage axial detents 52 with a spring force. A positive force must be manually applied to move the sheath from a first position in which the electrode tip 40 is exposed (shown in solid lines in FIG. 4.) to a second position in which the electrode tip 40 is covered by the sheath 42 (shown in dotted lines in FIG. 4). A barrel sleeve 32 with a disk shaped member on one end is positioned between the electrode adapter 34 and the sheath 42. The disk shaped member and the spring member 37 prevent the sheath 42 from being over-extended.

The surgical tool 20 is rotatable relative to the handle 10. The electrode adapter 34 is round and the releasable latch 56 has a round aperture therethrough thereby permitting rotation of the surgical tool 20. When the sheath 42 is in the first position, ratchet teeth engaging buttons 48 located on each spring bar 37 engage the ratchet teeth 50 to provide rotational latching as the surgical tool 20 is rotated. The spring bars 37 provide a biasing force to engage the ratchet teeth 50.

Having described the invention, what is claimed is:

1. A multi-functional surgical instrument comprising:

a handle;

an interchangeable surgical tool removably, rotatably attached to said handle wherein said surgical tool comprises:
   at least one electrode for electrosurgical cutting of tissue;
   a moveable sheath for covering the at least one electrode, said sheath being moveable from a first axial position to a second axial position; and a means adapted to contact said sheath for latching said sheath in one of said axial positions;
   means for indexing the interchangeable surgical tool to a plurality of discrete radial positions wherein said means for indexing is connected between said interchangeable surgical tool and said handle; and
   said surgical tool including at least one spring member, said at least one spring member providing a biasing force for said means for indexing and said means for latching.

2. The multi-functional surgical instrument according to claim 1, wherein the means for latching includes a tool attachment extension on the housing, the tool attachment extension having a first latching engagement member and a second latching engagement member for engaging said at least one spring member.

3. The multi-functional surgical instrument according to claim 1 wherein said means for indexing includes a tool attachment extension on said handle, said tool attachment extension having a plurality of ratchets about an outer peripheral surface and said at least one spring member engaging said plurality of ratchets.

4. The multi-functional surgical instrument according to claim 3, further comprising:

a ratchet engaging button on each of said at least one spring member.

5. The multi-functional surgical instrument according to claim 1 wherein said handle includes a releasable latch means for releasably engaging the surgical tool.

6. The multi-functional surgical instrument according to claim 5 wherein said releasable latch means forms an electrically conductive connection from an electrical source to said at least one electrode.

7. A multi-functional surgical instrument comprising:

a handle;

an interchangeable surgical tool removeably, rotatably attached to the handle wherein said surgical tool comprises:
   at least one electrode for electrosurgical cutting of tissue; a moveable sheath for covering said at least one electrode, said sheath being moveable from a first axial position to a second axial position;
   a means for latching said sheath in one of said axial positions, wherein said surgical tool includes at least one spring member, when said sheath is in the second axial position said at least one spring member providing a biasing force for the means for latching and when said sheath is in the first axial position said at least one spring member providing a biasing force for both the means for latching and the means for indexing; and
   means for indexing said interchangeable surgical tool to a plurality of discrete radial positions.

8. A multi-functional surgical instrument comprising:

an electrically insulating housing having a tool attachment extension thereon, the tool attachment extension having a plurality of ratchets and first and second latch engagement members about an outer peripheral surface, the first latch engagement member being axial spaced from the second engagement member;

a releasable latch means on said housing for releasably engaging an interchangeable surgical tool;

a fluid irrigation tube in said housing and a valve for controlling the flow of fluid through the fluid irrigation tube;

a fluid evacuation tube in said housing and a valve for controlling the flow of fluid through the fluid evacuation tube;

an interchangeable surgical tool comprising: an electrically conductive annular tube; an electrical conductive interface fitting attached to a first end of the annular tube; an electrode for electrosurgical cutting of tissue attached to a second end of the annular tube; a moveable sheath, the sheath being moveable from a first position to a second position relative to said annular tube, when in the second position the sheath covering the electrode; and a spring means for engaging the ratchets and the first and second latch engagement members;

the interface fitting adapted to fit into said releasable latch means having an axially extending bore there-through and a groove around the exterior of the interface fitting, the fluid irrigation tube and fluid evacuation tube being in fluid communication with the electrically conductive annular tube and the releasable latch means engaging the groove of the interface fitting, the releasable latch means forming an electrically conductive connection from an electrical source to the electrically conductive interface fitting.

\* \* \* \* \*